United States Patent [19]

Poskitt

[11] 4,114,090
[45] Sep. 12, 1978

[54] ELECTRONIC MOISTURE METER

[75] Inventor: Walter Edward Poskitt, St. Basile le Grande, Quebec, Canada

[73] Assignee: IMASCO Limited, Montreal, Canada

[21] Appl. No.: 715,170

[22] Filed: Aug. 17, 1976

[51] Int. Cl.² .......................................... G01R 27/26
[52] U.S. Cl. ............................................. 324/61 QS
[58] Field of Search ............ 324/61 QS, 61 R, 61 QL

[56] References Cited
U.S. PATENT DOCUMENTS

| | | | |
|---|---|---|---|
| 3,279,249 | 10/1966 | Tocanne | 324/61 R X |
| 3,295,042 | 12/1966 | Evalds et al. | 324/61 R X |
| 3,323,352 | 6/1967 | Branson | 324/61 QS |
| 3,684,952 | 8/1972 | Lundstrom | 324/61 QS |
| 3,777,258 | 12/1973 | Wochnowski | 324/61 QS |
| 3,793,585 | 2/1974 | Wilska | 324/61 QS |

*Primary Examiner*—Stanley T. Krawczewicz

[57] ABSTRACT

A moisture detection unit for sensing the moisture content of tobacco is disclosed. A capacitor sensor forming part of a C.R. network is arranged so that the tobacco is passed through or near the sensor. The capacitance of the sensor is proportional to the moisture content of the tobacco, and this capacitance determines the frequency derived by an oscillator to which the C.R. network is connected. The output frequency is inversely proportional to the sensor capacitance. A frequency to voltage converter derives a voltage proportional to the frequency and this voltage signal is then passed through an inverter. The inverter has an off-set which compensates for the standing capacitance of the sensor, to derive an output voltage which is proportional to the moisture content of the tobacco. This voltage can then be used to drive a digital read-out. Additionally, this voltage may be fed to control equipment associated with the tobacco water spray for varying the amount of water sprayed in accordance with the value of the voltage.

10 Claims, 1 Drawing Figure

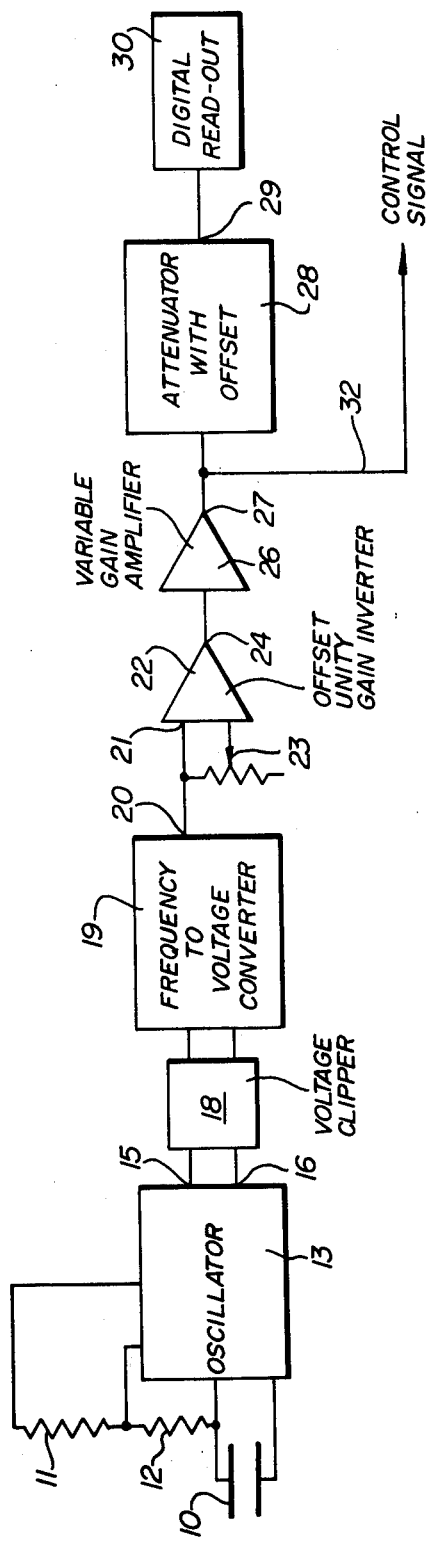

ELECTRONIC MOISTURE METER

BACKGROUND OF THE INVENTION

This invention relates to dielectric constant detection unit for detecting a change in the dielectric constant of a material.

The dielectric constant of materials is known to vary according to moisture content and this offers a useful possibility of measuring the moisture content of these materials, this information being required in the processing of tobacco, for example.

DESCRIPTION OF THE KNOWN ART

Moisture meters are known in which a capacitor sensor or electrode is maintained in the vicinity of material the moisture content of which is to be measured. Such meters are based on the fact that the capacitance of the sensor varies according to the presence of foreign material and more particularly, the capacitance is directly proportional to the moisture content of the material.

Various techniques are used for measuring the capacitance change due to moisture. One technique involves connecting a high frequency oscillator (2 MHZ) to the capacitor sensor and measuring the current flow through the sensor. No known technique involves the direct conversion of the oscillator frequency to a voltage indicative of the moisture content.

SUMMARY OF THE INVENTION

It is an object of the present invention to provide a simple device capable of detecting changes in the dielectric constant of materials.

In particular it is an object of the invention to provide such a device which uses the variation in frequency of an oscillator circuit to derive a signal proportional to the dielectric constant of the material.

It is a further object to provide a moisture meter detecting changes in the moisture content of materials.

According to the broadest aspect of the present invention, there is provided a dielectric constant detection unit for detecting a change in the dielectric constant of a material, comprising a capacitor sensor the capacitance of which varies according to the nature and quality of the material in the vicinity of the sensor, the sensor forming part of a C.R. network connected to an oscillator means which derives an output signal the frequency of which is inversely proportional to the capacitance of the capacitor sensor, a frequency to voltage converter connected to the oscillator and an inverter connected to the frequency to voltage converter, the inverter deriving an output signal proportional to the capacitance of the capacitor sensor.

According to a more particular aspect of the present invention, there is provided a moisture detection unit comprising a capacitor sensor for sensing the moisture content of material in the vicinity of the sensor, the sensor forming part of a C.R. network connected to an oscillator means which derives an output signal the frequency of which is inversely proportional to the capacitance of the capacitor sensor, a frequency to voltage converter connected to the oscillator and an inverter connected to the frequency to voltage converter, the inverter deriving an output signal proportional to the capacitance of the capacitor sensor.

BRIEF DESCRIPTION OF THE DRAWINGS

The present invention will now be described in greater detail with reference to the accompnying drawing which is a block diagram of a moisture meter according to the invention.

DESCRIPTION OF THE PREFERRED EMBODIMENT

The moisture meter includes a capacitor 10 and resistors 11 and 12 connected to inputs of a 0 to 10 KHZ oscillator 13. The capacitor, which in this specific embodiment is shown as a double plate type, is, in practice, arranged so that the material the moisture content of which is being measured passes through or near the capacitor. Thus, the material of the capacitor must be chosen such that it will not be adversely affected by the material being measured. Furthermore the standing capacitance of the capacitor should be of a value which will make a small change in the range 10–200 pf detectable.

The capacitance of the capacitor is directly dependent on the moisture content of the material being measured, and the time constant of the C.R. network comprising the capacitor 10 and resistors 11 and 12 is directly proportional to this capacitance.

The oscillator 13 derives a square wave output at terminals 15 and 16 of a frequency which varies inversely with changes in the time constant of the C.R. network. The oscillator is calibrated to give a 10 KHZ 10 volt square wave when no material is sensed by the capacitor thereby limiting the output signal to 10 volts D.C. The capacitor may, typically, have a capacitance of 30 pf in this case and the calibration is effected by selecting (or adjusting) suitable values for resistors 11 and 12.

The resultant square wave is passed through a voltage clipper 18 which removes any supply noise from the oscillator signal and gives square wave of 6.5 volts. This 6.5 volt wave is passed to the inputs of a frequency to voltage converter 19 which derives at its output 20 a voltage which is directly dependent on the input frequency. A suitable frequency to voltage converter is the TELEDYNE PHILBRICK model 4702 which provides excellent linearity in the low frequency range used. The frequency to voltage converter preferably is adjusted to give a 10 volt DC output for the 10 KHZ input.

The 10 volt DC output is passed to one input 21 of an offsetting unity gain inverter 22 forming the first stage of a three stage amplifier. To compensate for the signal corresponding to the standing capacitance of the sensor, the inverter 22 has an off-set input 23 which may be set at +10 volts DC to derive at the output 24 of the inverter 0 volts which represents the calibrated zero for a variable gain amplifier 26 connected to the output 24.

The variable gain amplifier 26 increases the output signal of inverter 22 to a voltage of 0–10 volts DC. Obviously, in the calibrated condition, the signal derived at the output 27 of the amplifier 26 is zero.

The output 27 is connected to an attenuator and off-set 28 which converts the 0–10 volt DC input to a value at its output 29 which will operate the following digital read-out 30; the off-set ensures that there is a reading on the digital read-out 30 representing the absolute value of the moisture content of the material being measured.

Also connected to the output 27 is a control signal line which may be used with electronic control equipment (not shown) to vary the quantity of moisture being added to the material being measured.

In operations, as material, such as tobacco, is passed near the capacitor, the frequency of the output signal derived by the oscillator 13 is determined by the moisture content of the tobacco. This frequency determines the voltage derived at the output 20 of the frequency to voltage converter 19 which, in turn, sets the voltage appearing at the inverter output 24. This causes the value of the moisture content to be displayed on the digital readout.

As indicated above, the voltage appearing at amplifier output 27 may be conveyed along line 32 and, if it does not represent a desired moisture value as set on the electronic control equipment the electronic control equipment will send an appropriate instruction to a water spray.

What I claim as my invention is:

1. A moisture detection unit comprising:
   a capacitor sensor for sensing the moisture content of the material the moisture content of which is to be detected and which is positioned in the vicinity of the sensor, said capacitor sensor attaining a value of capacitance proportional to that moisture content;
   at least one resistor interconnected with said capacitor sensor to form a resistance-capacitance network;
   a free-running oscillator means connected to said resistance-capacitance network for producing an output signal the frequency of which is inversely proportional to the capacitance of said capacitor sensor and is from 0 to 10 KHz;
   a frequency-to-voltage converter connected to said free-running oscillator means for producing a D.C. voltage proportional to the frequency of the output signal of said free-running oscillator means; and
   an inverter connected to said frequency-to-voltage converter for producing an output voltage inversely proportional to the D.C. voltage of the frequency-to-voltage converter and directly proportional to the moisture content of the material.

2. A moisture detection unit as claimed in claim 1, in which:
   said inverter has an off-set adjustment means for adjusting the output of said inverter so that a predetermined capacitance of said capacitor sensor causes a zero output voltage.

3. A moisture detection unit as claimed in claim 2, in which:
   said predetermined capacitance of the capacitor sensor is the standing capacitance of the capacitor sensor in the absence of material in the vicinity of the capacitor sensor.

4. A moisture detection unit as claimed in claim 3, further comprising:
   a read-out means connected to said inverter for producing an output signal calibrated in terms of the moisture content of the material.

5. A moisture detection unit as claimed in claim 3, further comprising:
   a control means coupled to said inverter for changing the moisture content of the material in response to the output voltage of said inverter.

6. A moisture detection unit as claimed in claim 5, further comprising:
   a variable gain amplifier having input connected to the output of said inverter and having an output connected to the input of said control means, for coupling said control means and said inverter.

7. A moisture detection unit as claimed in claim 6, further comprising:
   an attenuator means connected to the output of said variable gain amplifier for producing an output proportional to the absolute value of the moisture content of the material in the vicinity of the capacitor sensor; and
   a read-out means connected to said attenuator means for producing an output signal calibrated in terms of the moisture content of the material.

8. A moisture detection unit as claimed in claim 1, further comprising:
   a read-out means connected to said inverter for producing an output signal calibrated in terms of the moisture content of the material.

9. A moisture detection unit as claimed in claim 1, in which:
   said frequency-to-voltage converter contains a voltage clipper to restrict the voltage range of the output signal received from said oscillator means.

10. A dielectric constant detection unit, comprising:
    a capacitor sensor for detecting the dielectric constant of the material the dielectric constant of which is to be detected and which is positioned in the vicinity of the sensor, said capacitor sensor attaining a value of capacitance proportional to the dielectric constant;
    at least one resistor interconnected with said capacitor sensor to form a resistance-capacitance network;
    a free-running oscillator means connected to said resistance-capacitance network for producing an output signal the frequency of which is inversely proportional to the capacitance of said capacitor sensor and is from 0 to 10 KHz;
    a frequency-to-voltage converter connected to said free-running oscillator means for producing a D.C. voltage proportional to the frequency of the output signal of said free-running oscillator means; and
    an inverter connected to said frequency-to-voltage converter for producing an output voltage inversely proportional to the D.C. voltage of the frequency-to-voltage converter and directly proportional to the dielectric constant of the material.

* * * * *